(12) United States Patent
Mercier et al.

(10) Patent No.: US 7,754,775 B2
(45) Date of Patent: Jul. 13, 2010

(54) MULTI-LAMELLAR LIQUID CRYSTAL EMULSION SYSTEM

(76) Inventors: Michel F. Mercier, 925 Mountain Ave., P.O. Box 1162, Mountainside, NJ (US) 07082-1162; Paul Thau, 181 Dogwood La., Berkeley Heights, NJ (US) 07922; John Chase, 12 Encampment Dr., Bedminster, NJ (US) 07921

( * ) Notice: Subject to any disclaimer, the term of this patent is extended or adjusted under 35 U.S.C. 154(b) by 1600 days.

(21) Appl. No.: 10/830,568

(22) Filed: Apr. 23, 2004

(65) Prior Publication Data

US 2005/0238677 A1    Oct. 27, 2005

(51) Int. Cl.
*A61K 8/06*    (2006.01)
(52) U.S. Cl. .................. 514/943; 514/988; 424/401
(58) Field of Classification Search .............. 424/401; 514/943
See application file for complete search history.

(56) References Cited

U.S. PATENT DOCUMENTS

| | | | |
|---|---|---|---|
| 5,429,820 | A | 7/1995 | Kamitani et al. |
| 5,603,940 | A | 2/1997 | Candau et al. |
| 5,658,575 | A | 8/1997 | Ribier et al. |
| 5,866,111 | A | 2/1999 | Felardos et al. |
| 5,925,364 | A | 7/1999 | Ribier et al. |
| 6,077,816 | A | 6/2000 | Puvvada et al. |
| 6,709,663 | B2 | 3/2004 | Espinoza |
| 6,831,107 | B2 * | 12/2004 | Dederen et al. ............. 514/777 |

FOREIGN PATENT DOCUMENTS

| FR | 2 802 805 A1 | 6/2001 |
|---|---|---|
| WO | WO 97/05857 A1 | 2/1997 |
| WO | WO 01/34100 A1 | 5/2001 |

OTHER PUBLICATIONS

Flick, E., Cosmetics Additives, Noyes Publications, 1991, pp. 183-184.*
Sisterna, "Sisterna® Sucrose Esters in Oil-in-Water Emulsions," 6 pages. (Mar. 1999).
Sisterna, "Sucrose Esters of Fatty Acids: The Route to Mildness" 15 pages. (Mar. 2003).
Gao, T. et. al., "Sunscreen Formulas with Multilayer Lamella Structure," Cosmetics & Toiletries Magazine, vol. 118, No. 10, pp. 41-44 (Oct. 2003).
Eccleston, G., "Multiple-phase oil-in-water emulsions," J. Soc. Cosmet. Chem., vol. 41, pp. 1-22 (Jan./Feb. 1990).
Sadtler V., et al., Shear-induced phase transitions in sucrose ester surfactant, Journal of Colloid and Interface Science, vol. 270, pp. 270-275 (2004).
Gallegos, C. et al., ACS Symposium Series: Structure and Flow in Surfactant Solutions, Chapt. 14—Rheology of Sucrose Ester Aqueous Systems, pp. 217-228 (1994).
New Paradigm Technologies, "BIOBASE™—A New, Formulator-Friendly Self-Emulsifying Base with Exceptional Mildness" 9 pages. (undated).
Seppic, "Montanov—Emulsifiers in Harmony with Nature" 8 pages. (Jul. 2000).
International Specialty Products, "Prolipid™ 141 for Skin Care," 8 pages. (Apr. 1999).
ICI Surfactants, "Arlatone 2121: Natural emulsifier for oil-in-water milks and creams," 4 pages (undated).
Lecocu, N. et al., "Glucolipids Liquid Crystal Promoters" 10 pages. (undated, published by SEPPIC, Paris, France).
Seppic, "Montanol® 68—A Glucolipid of Vegetable Origin" 16 pages. (Jan. 1991).
Loll, P. "Liquid Crystals in Cosmetics Emulsions," 23 pages (Reprint of paper presented at In-Cosmetics Conference, London, UK, Mar. 3-5, 1993).
Ribeiro, H.M. et al., "Structure and rheology of semisolid o/w creams containing cetyl alcohol/non-ionic surfactant mixed emulsifier . . . ", Int'l J Cosm Sci, 26: 47-59 (2004).
Sisterna, "New Applications for: Super Mild & Safe Sucrose Esters," 33 presentation slides (Sep. 2002).
Sisterna, "Sisterna Sucrose Esters—A Novel Range of Multifunctional Raw Materials," 70 presentation slides (Mar. 2003).

* cited by examiner

*Primary Examiner*—Gina C Yu
(74) *Attorney, Agent, or Firm*—Louis C. Paul & Associates, PLLC

(57) ABSTRACT

Topical cosmetic and pharmaceutical oil-in-water emulsions wherein an emulsifier blend, comprising a mixture of at least two sucrose esters in combination with at least one solid fatty alcohol, forms a multi-lamellar liquid crystalline network that effectively moisturizes and protects the skin, and provides a useful vehicle for delivery of active ingredients. Sucrose esters are used in emulsions of the present invention at very low concentrations (from about 0.2 % to about 1.2 % by combined weight of sucrose esters relative to the total weight of the emulsion).

15 Claims, 2 Drawing Sheets

MULTI-LAMELLAR LIQUID CRYSTAL EMULSION SYSTEM

CROSS-REFERENCE TO RELATED APPLICATIONS

Not Applicable.

STATEMENT REGARDING FEDERALLY-SPONSORED RESEARCH OR DEVELOPMENT

Not Applicable.

FIELD OF THE INVENTION

The present invention relates to topical cosmetic and pharmaceutical compositions. More particularly, the invention relates to stable cosmetic and pharmaceutical oil-in-water emulsions wherein an emulsifier blend, comprising a mixture of at least two sucrose esters in combination with at least one solid fatty alcohol, forms a multi-lamellar liquid crystalline network. The present invention gives formulators the ability to use very low concentrations of sucrose esters (from about 0.2% to about 1.2% by combined weight of sucrose esters relative to the total weight of the emulsion) to prepare aesthetically elegant and functional cosmetic formulations, including skin moisturizers, skin protectants and water-resistant sunscreens, as well as topical delivery vehicles for immediate and sustained release of active ingredients to the skin.

BACKGROUND OF THE INVENTION

The stratum corneum, the outermost layer of the epidermis, is comprised of corneocytes surrounded by a matrix of hydrophobic lipid membranes arranged in multiple lamellar sheets. Structurally, the stratum corneum is analogized to a brick and mortar wall, with anucleated cells as "bricks" and the intercellular lamellar membranes as "mortar". The sheets of lamellar membranes have a crystal-like periodic arrangement, and readily slide over one another, thus keeping the brick and mortar wall pliant and elastic.

The stratum corneum serves important barrier functions, foremost of which is preventing excessive transepidermal water loss ("TEWL"). In addition to retarding TEWL, the sheets of the lipid lamellar membranes also protect against ingress of foreign chemicals and microorganisms.

Emulsifiers that form lamellar liquid crystals are marketed by cosmetic ingredient suppliers as mimicking the multi-lamellar lipid structure of the stratum corneum. See, e.g. Seppic, "Montanov: Emulsifiers in Harmony with Nature", p. 1 (July 2000) ("Montanov"); New Paradigm Technologies "Biobase™ S: Product Information," p. 1 (Undated) ("Biobase"); International Specialty Products, "Prolipid™ 141 For Skin Care," pp. 3, 4 (April 1999) ("Prolipid"). Because they are biomimetic, lamellar liquid crystals serve barrier and water-retention functions.

Pioneering theoretical work on the formation of lamellar liquid crystalline networks was done by Friberg and Barry in the early 1970s and is summarized in a Technical Note entitled "Sisterna Sucrose Esters in Oil-in-Water Emulsions" published in March 1999 ("Sisterna Technical Note"). As summarized in the Technical Note, lamellar liquid crystal networks can be formed in oil-in-water emulsions by combining a high HLB primary emulsifier (i.e., a hydrophilic swellant) and a second, low-to-medium HLB, co-emulsifier (i.e., a hydrophobic gellant). The high HLB primary emulsifier reduces interfacial tension and facilitates the formation of small oil droplets in the outer aqueous phase. The low HLB co-emulsifier forms a gel network. This network structure stabilizes the emulsion by preventing creaming and coalescence of the oil droplets as well as by building viscosity. More specifically, by heating the water phase to above the melting point of the low HLB co-emulsifier, the fatty chains of the co-emulsifier parallel each other, forming a bi-layer structure—a lamellar phase. When subsequently cooled below that melting point, gel networks form around the co-emulsifier fatty chains.

Commercially available emulsifier systems that produce lamellar liquid crystals are known in the art. Sisterna, for example, markets a line of sucrose esters for this purpose. See, Sisterna, "Sucrose Esters of Fatty Acids: The Route to Mildness" (March 2003) ("Sisterna Formulation Guide"); see also Sisterna Technical Note, supra. The Sisterna Formulation Guide discloses six sample formulae which use a combination of two sucrose esters: A.01—Cream Foundation; C.12—Basic Emulsion (O/W); C.13—Eye Cream with Vitamin A; C.21—Regenerating Night Cream; L.08 Moisturizing After Shave Balm; and L. 14—Natural Basic Lotion. However, none of these formulae teach or suggest using the mixture of two sucrose esters in combination with at least one solid fatty alcohol as in the present invention. Sample formula C.12, for example, discloses the use of sucrose monostearate and sucrose distearate in combination with a octyldodecanol—a branched chain liquid fatty alcohol. Liquid fatty alcohols do not form lamellar liquid crystal gel networks of the type of the present invention.

In addition to Montanov, Biobase and Prolipid 141, discussed supra, Arlatone 2121 and Montanol 68, manufactured by ICI Surfactants and Seppic, respectively, also form lamellar liquid crystalline networks. Arlatone 2121 comprises a single sucrose ester (i.e., sucrose cocoate) in combination with sorbitan stearate. See, Uniqema "Liquid Crystals in Cosmetic Emulsions" (March 1993). However, none of these prior-art products teach a stable oil-in-water emulsion wherein an emulsifier blend comprising a mixture of at least two sucrose esters in combination with at least one solid fatty alcohol forms a lamellar liquid crystalline network.

Surprisingly, the emulsion system of the present invention produced a dense liquid-crystalline gel network by using a mixture of sucrose esters (i.e., without additional emulsion stabilizers) in combined amounts of less than about 1% by weight relative to the total weight of the emulsion. Indeed, a stable emulsion surprisingly can be produced using the mixture of sucrose esters at a combined concentration of as low as from about 0.2% to about 0.3% by weight relative to the total weight of the emulsion. Sample Formula L.08 in the Sisterna Formulation Guide teaches a combined amount of 1.3% sucrose esters relative to the total weight of the composition. However, unlike the multi-lamellar liquid crystal emulsion system of the present invention, the L.08 emulsion was appreciably stabilized by the addition of a significant amount Carbomer.

The use of solid fatty alcohols to promote lamellar phase formation in oil-in-water emulsions is taught in the prior art with respect to specific emulsifier systems that do not use sucrose esters. See, e.g., Prolipid, p. 2 (use of behenyl, lauryl, myristyl and cetyl alcohols to aid in formation of lamellar phase in an emulsifier system also consisting of glyceryl stearate, stearic acid, palmitic acid and lecithin); Montanov, p. 1 (combination of solid fatty alcohols and glucosides); Biobase, p. 1 (glyceryl stearate, cetearyl alcohol and sodium stearoyl lactylate).

The use of a solid fatty alcohol, cetearyl alcohol, in a sucrose ester emulsifier system that forms lamellar liquid crystal networks is taught at page 4 of the Sisterna Technical Note. However, that publication teaches the combination of solid fatty alcohol with a single sucrose ester, not a mixture of two sucrose esters. Moreover, the Sisterna Technical Note neither teaches nor suggests a mixture of at least two sucrose esters in combination with at least one solid fatty alcohol at the low combined levels of sucrose esters of the present invention.

U.S. Pat. Nos. 5,925,364 and 5,658,575 also describe the formation of lamellar liquid crystals using sucrose distearate. However, these patents neither teach nor suggest combining a mixture of two sucrose esters with a solid fatty alcohol. Additionally, these patents do not teach or suggest hydrating the blend comprising a mixture of two sucrose esters and at least one solid fatty alcohol prior to adding the oil phase to the outer aqueous phase.

Patent application WO 01/34100 teaches oil-in-water emulsions capable of forming liquid crystals in water comprising as an essential ingredient at least one polyhydric alcohol at levels greater than about 20%. This application neither teaches nor suggests combining a mixture of two sucrose esters with a solid fatty alcohol.

Sucrose esters are known to be desirable for their mildness and safety. See, e.g., Sisterna Formulation Guide. However, they are expensive compared to other emulsifiers and, accordingly, are not used as widely as they might be at lower prices. Because the emulsifier system of the present invention is comprised of a mixture of sucrose esters at very, low levels (i.e., from about 0.2% to about 1.2% by combined weight of sucrose esters relative to the total weight of the emulsion), the present invention provides a cost-effective method for using sucrose esters. More particularly, even at such low levels, formulators have the ability to create stable cosmetic and topical pharmaceutical compositions of varying consistencies, from firm creams to light, atomizable lotions.

Emulsifier systems employed to maintain the stability of cosmetic or pharmaceutical compositions can indirectly cause irritation by disrupting the skin's outer lipid barrier, thus allowing irritants to penetrate the skin. Because the two sucrose ester emulsifiers of the present invention are present at very low levels (i.e., less than about 1.2% by combined weight relative to the total weight of the emulsion), the present invention meets the need of formulators for emulsion systems that minimizes disruption of the stratum corneum together with attendant penetration of skin irritants. Moreover, because the emulsifier blend of the present invention forms a biomimetic, multi-lamellar liquid crystal gel network, emulsions of the present invention serves to protect and strengthen the barrier created by the stratum corneum by keeping it pliant and elastic.

A related advantage of the present invention is the flexibility it affords formulators to use more skin compatible, less irritating preservative systems. More particularly, since the emulsion system of the present invention is non-ethoxylated, milder, hydroxy-based preservatives (e.g., methyl and propylparaben) can be used instead of harsher, formaldehyde-releasing preservative systems. Additionally, the anti-microbial activity of sucrose esters allows formulators to use lesser amounts of preservative, thereby further reducing the potential for skin irritation from preservatives.

The multi-lamellar liquid crystal gel network formed by emulsions of the present invention are more stable in comparison to other vesicular structures in cosmetic and pharmaceutical compositions (i.e., liposomes), thus meeting the need of formulators for stable, skin-compatible vehicles for topical delivery of active ingredients. The present invention also meets the need of formulators for delivery systems that are both versatile and aesthetically elegant. More particularly, the present invention allows formulators to prepare uniform dispersions of creams and lotions, both with high gloss, good surface spreading and water resistance.

SUMMARY OF THE INVENTION

The claimed invention is a novel oil-in-water emulsifier system for application to the skin wherein low concentrations (from about 1% to 4% on a weight/weight basis) of an emulsifier blend comprising a mixture at least two sucrose esters in combination with at least one solid fatty alcohol and, optionally, a phytosterol, forms a dense lamellar liquid crystalline network which effectively moisturizes and protects the skin, and provides a useful vehicle for topical delivery of active ingredients.

DRAWINGS

DETAILED DESCRIPTION OF THE INVENTION

Figure 1:
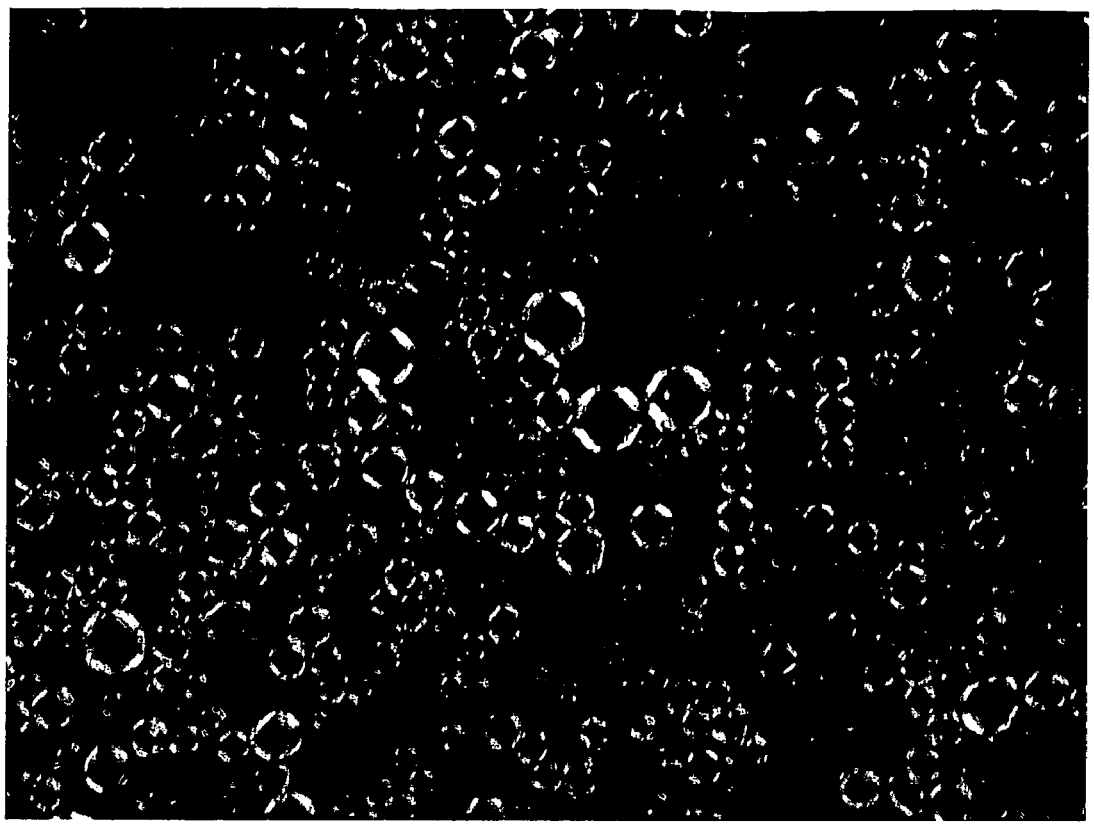
FIG. 1 shows a multi-lamellar liquid crystal emulsion system of the present invention under polarized light(200×).

The present invention relates to a novel, stable oil-in-water emulsion wherein an emulsifier blend, comprising a mixture of at least two sucrose esters in combination with at least one solid fatty alcohol and, optionally, a phytosterol, forms a multi-lamellar liquid crystal gel network. Low concentrations of the mixture of sucrose esters (on a combined weight/weight basis) unexpectedly have been found to produce stable emulsions over a range of viscosities, with distinctive rheological and aesthetic characteristics.

More particularly, a multi-lamellar liquid crystal gel network is formed in the oil-in-water emulsion of the present invention by using the emulsifier blend at concentrations from about 0.5% to about 5% weight/weight. Preferably, the blend is used at levels of from about 2% to about 4% weight/weight. The blend is comprised of (i) from about 20% to about 50% weight/weight of a mixture of at least two sucrose esters, one being a monoester sucrose-R and the other being a diester sucrose-$R_1R_2$ wherein each of $R_1$ and $R_2$ is independently selected from aliphatic hydrocarbons having from about 12 to about 22 carbon atoms and (ii) from about 50% to about 80% of a solid fatty alcohol. In a preferred embodiment, from about 20% to about 30% of the blend is comprised of a mixture of two sucrose esters—one a monostearate (e.g. Sisterna® SP70-C, available through MMP, Inc., South Plainfield, N.J.), the other a distearate (e.g., Sisterna® SP70-C, also available through MMP, Inc.). The remaining portion of the preferred embodiment of the emulsifier blend is comprised of from about 70% to about 80% weight/weight of at least one solid fatty alcohol.

The ratio of the two sucrose esters, expressed as pure sucrose monoester, preferably sucrose monostearate, to pure sucrose diester, preferably sucrose distearate, ranges from 1:0.75 to 1:1.33, with a particularly preferred ratio of 1:1.13, on a weight/weight basis. Commercially available sucrose monoester, preferably sucrose monostearate, is predominantly composed of the monoester, but may also contain lesser amounts of other esters. Commercially available sucrose diester, preferably sucrose distearate, is predominantly composed of the diester, but may also contain lesser amounts of other esters. Thus, the monoester content of one sucrose monostearate suitable for use in the present invention is from about 60% to about 80% pure sucrose monostearate, while the pure sucrose distearate content of this material is less than about 40%, typically less than about 30%. The diester content of one sucrose distearate suitable for use in the present invention is from about 40% to about 60% pure sucrose distearate, typically about 50-55%, while the pure sucrose monostearate content of this material is less than about 40%, typically less than about 35%. The diester material may also contain up to about 20% of higher esters, typically, but not limited to triester and tetraester. Sisterna® SP70-C, a preferred sucrose monostearate, is comprised of 70% monoester, 25% diester and 5% triester. Sisterna® SP30-C, a preferred sucrose distearate, is comprised of 30% monoester, 52% diester, 16% triester and 2% tetraester.

The inner oil phase may range from about 0.5% to about 35% by weight relative to the total weight of the emulsion. Oils suitable for use in the present invention include, cosmetically acceptable hydrocarbon-based oils, mineral oil, petrolatum, polydecene, polyolephins, glycerides, silicone oils and cosmetic esters. Non-limiting examples of optional oil phase ingredients include lanolin, lecithin and natural oils.

The aqueous phase of the present invention may range from about 65% to about 95% by weight relative to the total weight of the emulsion. The aqueous phase may contain water or a mixture of water and polyhydric alcohol(s), such as, for example, glycerol, glycols, as well as water-soluble ingredients well know in the art.

Small percentages of thickener, from about 0.05% to about 0.5% weight/weight may be added to the water phase to help achieve the desired viscosity. Thickeners suitable for use in the present invention are well-known in the cosmetic art and include acrylic acid polymers of the Carbomer family, hydrophobically-modified polymers, such as Pemulen® (Noveon Personal Care) and Aculyn™ (Rohm and Haas), xanthan gum, guar gum, and magnesium aluminum silicate, preferably a hydrophobically-modified polymers thickener, xanthan gum or guar gum. In a preferred subset of embodiments, Carbomer is limited to a concentration not in excess of 0.25% weight/weight, more preferably not in excess of 0.2% weight/weight, and most preferably Carbomer is excluded. In some instances, a relatively insignificant amount of Carbomer may be present. For purposes of this application, a relatively insignificant amount of Carbomer shall mean an emulsion in which Carbomer is present at less than about 0.1 weight %.

Suitable medium-to-high HLB sucrose esters (i.e., HLB from about 10 to about 16) for use as swellants in the present invention include sucrose stearate, sucrose palmitate, sucrose cocoate and sucrose laurate. Preferred high HLB sucrose esters are sucrose stearate and sucrose palmitate. Low-to-medium HLB sucrose esters (i.e., HLB from about 2 to about 8) suitable for use in the present invention as gellants include the sucrose diester analogs of the foregoing monoesters, preferably the distearates. A preferred low HLB sucrose ester is sucrose distearate with a monoester content of about 30%.

Solid fatty alcohols suitable for use in the present invention are those having from about 16 to about 22 carbon atoms, preferably from about 16 to about 18 carbon atoms, and having a melting pointing of at least about 45° C. These solid fatty alcohols are typically straight-chained, although suitable materials may be branched. Non-limiting examples of solid fatty alcohols suitable for use in the present invention include cetyl alcohol, stearyl alcohol, behenyl alcohol, and mixtures thereof. Mixtures of cetyl and stearyl alcohol in a ratio of from about 30:70 to about 70:30 are a preferred solid fatty alcohol. A particularly preferred solid fatty alcohol is a mixture of cetyl and stearyl alcohols in a ratio of about 50:50.

A phytosterol may optionally be added to the blend at concentrations from about 0.05% to about 0.5% by weight relative to the total weight of the emulsion. These ingredients may serve to further promote formation of the lamellar liquid crystal gel network. A preferred phytosterol suitable for use in the present invention is beta sitosterol.

A variety of conventional hydroxy-based preservatives well-known in the art are suitable for use in the present invention. Non-limiting examples of such preservatives include methylparaben and propylparaben.

In order to produce the desired products, the basic components of the invention described above may be combined with other cosmetic or pharmaceutical ingredients which are well-known to cosmetic and pharmaceutical chemists. Examples of such additional components include, but are not limited to, antiseborrheic agents, anti-acne agents, antioxidants, skin lightening agents, depigmenting agents, anti-wrinkle agents, vitamins, sunscreen agents, self-tanning agents, topical analgesics, anti-inflammatory agents, antipruritic agents, deodorants, as well as purely cosmetic ingredients, such as pigments, water soluble emollients, humectants, stabilizers and fragrances.

Surprisingly, the present invention gives formulators the ability to use very small levels of sucrose esters (i.e., from about 0.2% to about 1.2% by combined weight relative to the total weight of the emulsion) to create stable cosmetic and topical pharmaceutical compositions of varying consistencies, from firm creams to light, atomizable lotions. At levels of about from about 0.8% to about 1.2% of combined sucrose esters weight/weight, a firm cream is formed. A combined mixture of sucrose esters at about from about 0.5% to about 0.75% weight/weight produces a soft cream. From about 0.4% to about 0.6% of combined sucrose esters weight/weight produces a heavy lotion. Combined sucrose esters at from about 0.2% to about 0.3% weight/weight produces a light lotion.

The oil-in-water emulsion of the present invention is prepared according to principles and techniques generally known to those skilled in the cosmetic and pharmaceutical arts.

The emulsifier blend comprising a mixture of at least two sucrose esters and at least one solid fatty alcohol is prepared by first melting the solid fatty alcohol(s) and thereafter adding the remaining sucrose esters, and optionally, beta sitosterol. The ingredients are mixed until homogeneous at an elevated temperature of from about 75° C. to about 85° C. using conventional propeller or loop mixers well known in the art. The blend is then allowed to cool, at which time it has a white to off-white, wax-like appearance. Alternatively, the blend may be purchased under the tradename. Crystalcast™ from MMP, Inc (South Plainsfield, N.J.).

The oil phase is prepared in a separate vessel by heating the oil or oil-blend to about 70° C. to about 75° C. Thereafter, oil miscible or dispersible ingredients are added and mixed with medium loop or propeller mixing.

The aqueous phase is prepared as follows: First, water is heated to a constant temperature of from about 70° C. to about 80° C. Next, ingredients which are readily dispersible in water (e.g., xanthan gum, glycerin, and paraben preservatives) are combined in the water by medium loop mixing at from about 200 rpm to about 300 rpm. Lastly, the blend is added to the aqueous phase and allowed hydrate for about 15 minutes under medium loop mixing. Alternatively, a hydrate of the blend may be pre-made according to the above procedure and then combined with the oil phase as described below.

The water phase is then transferred to a homogenizer mixer, such as the Silverson L4RT homogenizer, where it is maintained at a constant temperature of from about 70° C. to about 80° C. and mixed for about five minutes at from about 3,000 rpm to about 6,000 rpm. The oil phase is then slowly added and mixed with the homogenizer under the same conditions (i.e., constant temperature at from about 3,000 rpm to about 6,000 rpm) for a period of time of from about 5 to about 10 minutes.

The resulting emulsion is then transferred back to a medium loop or propeller mixer (at from about 200 to about 300 rpm) and allowed to cool until about 45° C. to 50° C. Thereafter, the emulsion is transferred back to a homogenizer mixer operating at from about 3,000 rpm to about 6,000 rpm for 5 minutes. Finally, the emulsion is returned to loop or propeller mixing and allowed to cool to a temperature of about 35° C., at which time processing is completed. An alternate procedure is to use a homogenizer mixer throughout the process (i.e., in place of medium loop or propeller mixing).

The following examples are further illustrative of the present invention. The components and specific ingredients are presented as being typical, and various modifications can be derived in view of the foregoing disclosure within the scope of the invention.

EXAMPLE 1

Sunscreen

Figure 2:
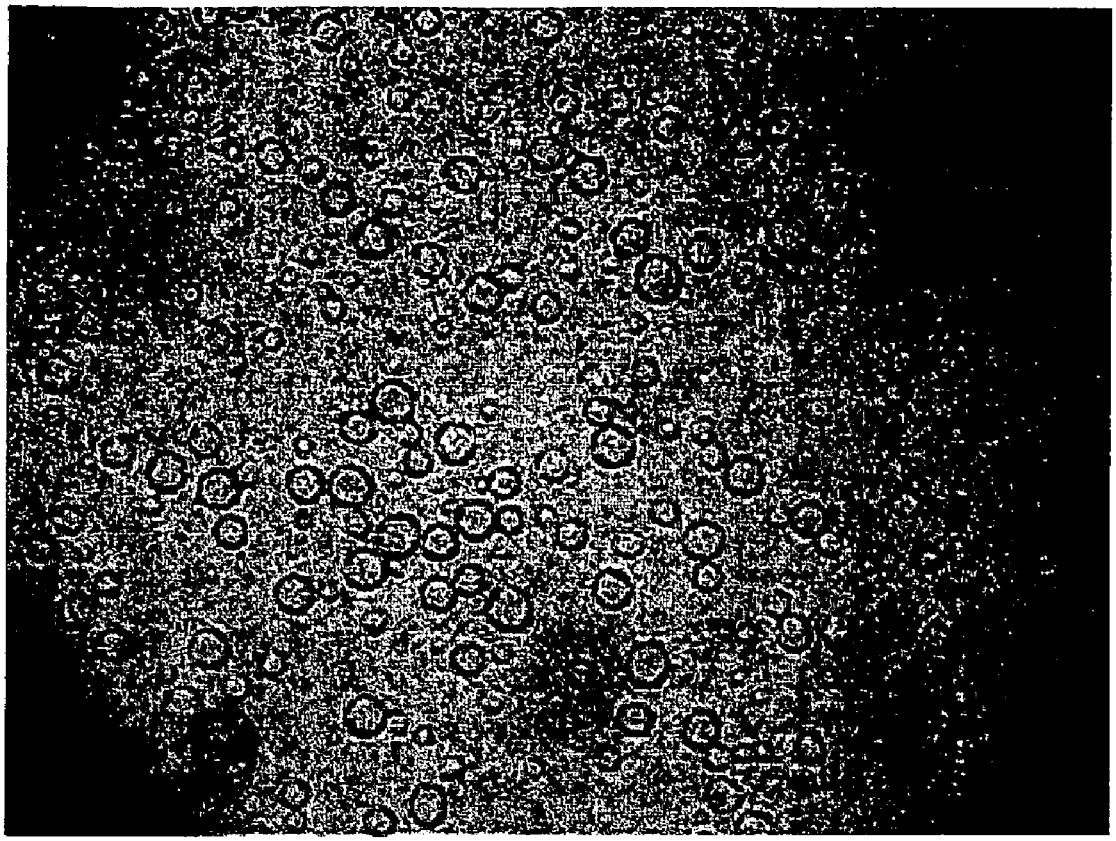
FIG. 2 shows a multi-lamellar liquid crystal emulsion system of the present invention under polarized light(video 200×).

A firm cream, oil-in-water sunscreen emulsion having a viscosity of 37,000 cps LV4@12 rpm and a pH of 6.48 was produced according to the procedure set forth above. The emulsion was stable at 40° C. for six weeks, at room temperature for six weeks, and after three freeze/thaw cycles. Figures is a photomicrograph of the emulsion of Example 1. FIG. 2 is a frame from a video of the emulsion of Example 1.

| Phase | Ingredient | % w/w |
| --- | --- | --- |
| Water | Water | 88.45 |
|  | Disodium EDTA | 0.10 |
|  | Glycerin | 2.00 |
|  | Xanthan Gum | 0.15 |
|  | Cetyl Alcohol | 1.47 |
|  | Stearyl Alcohol | 1.47 |
|  | Sucrose Stearate | 0.24 |
|  | Sucrose Distearate | 0.74 |
|  | Beta Sisterol | 0.08 |
|  | Methylparaben | 0.20 |
|  | Propylparaben | 0.10 |
| Oil | Octyl Methoxycinnamate | 5.00 |

EXAMPLE 2

Sunscreen

An oil-in-water sunscreen emulsion having a viscosity of 35,000 cps LV4@12 rpm and a pH of 6.44 was produced according to the procedure set forth above. The emulsion was stable at 40° C. for six weeks, at room temperature for six weeks, and after three freeze/thaw cycles.

| Phase | Ingredient | % w/w |
| --- | --- | --- |
| Water | Water | 76.95 |
|  | Disodium EDTA | 0.10 |
|  | Glycerin | 2.00 |
|  | Xanthan Gum | 0.15 |

-continued

| Phase | Ingredient | % w/w |
| --- | --- | --- |
|  | Cetyl Alcohol | 1.47 |
|  | Stearyl Alcohol | 1.47 |
|  | Sucrose Stearate | 0.24 |
|  | Sucrose Distearate | 0.74 |
|  | Beta Sisterol | 0.08 |
|  | Methylparaben | 0.20 |
|  | Propylparaben | 0.10 |
| Oil | $C_{12-15}$ Alkyl Benzoate | 6.00 |
|  | Octyl Methoxycinnamate | 7.50 |
|  | Butyl Methoxydibenzylmethane | 3.00 |

EXAMPLE 3

Delivery Vehicle

A soft cream, oil-in-water emulsion topical delivery vehicle having a viscosity of 28,000 cps LV4@12 rpm a pH of 6.37 was produced according to the procedure set forth above. The emulsion was stable at 40° C. for four weeks, at room temperature for four weeks, and after three freeze/thaw cycles.

| Phase | Ingredient | % w/w |
| --- | --- | --- |
| Water | Water | 82.95 |
|  | Disodium EDTA | 0.10 |
|  | Glycerin | 2.00 |
|  | Xanthan Gum | 0.15 |
|  | Cetyl Alcohol | 1.47 |
|  | Stearyl Alcohol | 1.47 |
|  | Sucrose Stearate | 0.24 |
|  | Sucrose Distearate | 0.74 |
|  | Beta Sisterol | 0.08 |
|  | Methylparaben | 0.20 |
|  | Propylparaben | 0.10 |
|  | Petrolatum | 5.00 |
| Oil | Caprylic/CapricTriglycerides | 5.00 |
|  | Tocopherol | 0.50 |

EXAMPLE 4

Makeup Remover

A soft cream, oil-in-water makeup remover emulsion having a viscosity of 25,000 cps LV4@12 rpm and a pH of 6.42 was produced according to the procedure set forth above.

| Phase | Ingredient | % w/w |
| --- | --- | --- |
| Water | Water | 69.95 |
|  | Disodium EDTA | 0.10 |
|  | Glycerin | 2.00 |
|  | Xanthan Gum | 0.15 |
|  | Cetyl Alcohol | 0.92 |
|  | Stearyl Alcohol | 0.92 |
|  | Sucrose Stearate | 0.15 |
|  | Sucrose Distearate | 0.46 |
|  | Beta Sisterol | 0.05 |
|  | Methylparaben | 0.20 |
|  | Propylparaben | 0.10 |
| Oil | Hydrogenated Polydecene | 20.00 |
|  | Caprylic/CapricTriglycerides | 5.00 |

EXAMPLE 5

Heavy Cream

A heavy cream, oil-in-water emulsion topical delivery vehicle having a viscosity of 35,000 cps LV4@12 rpm a pH of 6.57 was produced according to the procedure set forth above. The emulsion was stable at 40° C. for four weeks, at room temperature for four weeks, and after three freeze/thaw cycles.

| Phase | Ingredient | % w/w |
|---|---|---|
| Water | Water | 83.45 |
|  | Disodium EDTA | 0.10 |
|  | Glycerin | 2.00 |
|  | Xanthan Gum | 0.15 |
|  | Cetyl Alcohol | 1.47 |
|  | Stearyl Alcohol | 1.47 |
|  | Sucrose Stearate | 0.24 |
|  | Sucrose Distearate | 0.74 |
|  | Beta Sisterol | 0.08 |
|  | Methylparaben | 0.20 |
|  | Propylparaben | 0.10 |
| Oil | Petrolatum | 5.00 |
|  | Caprylic/CapricTriglycerides | 5.00 |

EXAMPLE 6

Soft Cream

A soft cream, oil-in-water emulsion topical delivery vehicle having a viscosity of 24,000 cps LV4@12 rpm a pH of 6.39 was produced according to the procedure set forth above. The emulsion was stable at 40° C. for four weeks, at room temperature for four weeks, and after three freeze/thaw cycles.

| Phase | Ingredient | % w/w |
|---|---|---|
| Water | Water | 84.95 |
|  | Disodium EDTA | 0.10 |
|  | Glycerin | 2.00 |
|  | Xanthan Gum | 0.15 |
|  | Cetyl Alcohol | 0.92 |
|  | Stearyl Alcohol | 0.92 |
|  | Sucrose Stearate | 0.15 |
|  | Sucrose Distearate | 0.46 |
|  | Beta Sisterol | 0.05 |
|  | Methylparaben | 0.20 |
|  | Propylparaben | 0.10 |
| Oil | Petrolatum | 5.00 |
|  | Caprylic/CapricTriglycerides | 5.00 |

EXAMPLE 7

Lotion

A lotion, oil-in-water emulsion topical delivery vehicle having a viscosity of 20,000 cps LV4@12 rpm a pH of 6.51 was produced according to the procedure set forth above. The emulsion was stable at 40° C. for four weeks, at room temperature for four weeks, and after three freeze/thaw cycles.

| Phase | Ingredient | % w/w |
|---|---|---|
| Water | Water | 85.44 |
|  | Disodium EDTA | 0.10 |
|  | Glycerin | 2.00 |
|  | Xanthan Gum | 0.15 |
|  | Cetyl Alcohol | 0.74 |
|  | Stearyl Alcohol | 0.74 |
|  | Sucrose Stearate | 0.12 |
|  | Sucrose Distearate | 0.37 |
|  | Beta Sisterol | 0.04 |
|  | Methylparaben | 0.20 |
|  | Propylparaben | 0.10 |
| Oil | Petrolatum | 5.00 |
|  | Caprylic/CapricTriglycerides | 5.00 |

EXAMPLE 8

Thin Lotion

A thin lotion, oil-in-water emulsion topical delivery vehicle having a viscosity of 7,500 cps LV4@ 12 rpm a pH of 6.41 was produced according to the procedure set forth above. The emulsion was stable at room temperature for four weeks and after three freeze/thaw cycles.

| Phase | Ingredient | % w/w |
|---|---|---|
| Water | Water | 86.44 |
|  | Disodium EDTA | 0.10 |
|  | Glycerin | 2.00 |
|  | Xanthan Gum | 0.15 |
|  | Cetyl Alcohol | 0.37 |
|  | Stearyl Alcohol | 0.37 |
|  | Sucrose Stearate | 0.06 |
|  | Sucrose Distearate | 0.19 |
|  | Beta Sisterol | 0.02 |
|  | Methylparaben | 0.20 |
|  | Propylparaben | 0.10 |
| Oil | Petrolatum | 5.00 |
|  | Caprylic/CapricTriglycerides | 5.00 |

EXAMPLE 9

Emulsifier Blend Hydrate

| Phase A | Ingredient | % w/w |
|---|---|---|
|  | Water | 91.91 |
|  | Disodium EDTA | 0.10 |
|  | Glycerin | 2.50 |
|  | Xanthan Gum | 0.19 |
|  | Cetyl Alcohol | 1.84 |
|  | Stearyl Alcohol | 1.84 |
|  | Sucrose Stearate | 0.30 |
|  | Sucrose Distearate | 0.92 |
|  | Beta Sisterol | 0.10 |
|  | Methylparaben | 0.20 |
|  | Propylparaben | 0.10 |

A hydrate of the blend of sucrose esters, solid fatty alcohols and beta sitosterol is made by combining, as Phase A, the ingredients listed above according to the following procedure: Make a slurry with Glycerin and Xanthan Gum in a main vessel. Add Water, Disodium EDTA, Methylparaben and Propylparaben to the main vessel. Mix with medium loop mixing at from about 200 rpm to about 300 rpm. Start heating. Add the emulsifier blend, made separately according to the procedure set out above or purchased as Crystalcast™, to the main vessel. Continue heating to 70° C.-80° C. Hold at a constant temperature for about 15 minutes. Stop heating. Switch to a homogenizer; homogenize for 5 to 10 minutes. Mix with medium loop mixing, start cooling. Shutdown at 35° C.

Calculate the amount of oil Phase B, consisting of Caprylic/Capric Triglyceride, needed to form an oil-in-water emulsion, where the oil phase constitutes 10% weight/weight. Mix Phase A with loop mixing at 450 rpm. Slowly add Phase B to the main vessel. Mix thoroughly. For increased viscosity homogenize. The emulsion of Example 4 can be made at ambient or room temperature.

The invention claimed is:

1. A topical cosmetic or dermatological composition comprising an emulsifier system that forms a multi-lamellar liquid crystalline network, said emulsifier system comprising:
   (a) 0.2% to about 1.2 wt % of a mixture of
      (i) a first sucrose ester being sucrose monostearate and
      (ii) a second sucrose ester being sucrose distearate; and
   (b) at least one solid fatty alcohol, said solid fatty alcohol having a melting point of at least about 45° C., wherein the ratio of monostearate to distearate is about 1:1.3.

2. A topical cosmetic or dermatological composition according to claim 1 wherein the at least one solid fatty alcohol is a mixture of cetyl and stearyl alcohols.

3. A topical cosmetic or dermatological composition having a multi-lamellar liquid crystalline network in an oil-in-water emulsion comprising:
   (a) a mixture of sucrose monoester and sucrose diester in a monoester to diester ratio of about 1:1.33, where the combined sucrose esters are present from about 0.2% to about 1.2% by weight relative to the total weight of the emulsion;
   (b) at least one solid fatty alcohol selected from the group consisting of cetyl alcohol, stearyl alcohol, behenyl alcohol, and mixtures thereof, where said solid fatty alcohol(s) is present at from about 0.7% to about 3.2% by weight relative to the total weight of the emulsion; and
   (c) optionally, beta sitosterol present at from about 0.05% to about 0.5% by weight relative to the total weight of the emulsion.

4. A topical cosmetic or dermatological composition according to claim 3 wherein the at least one first sucrose monoester is selected from the group consisting of sucrose monostearate, sucrose monopalmitate, sucrose monococoate, sucrose monolaurate, and mixtures thereof; and the at least one second sucrose ester is selected from the group consisting of sucrose distearate, sucrose dipalmitate, sucrose dicocoate, sucrose dilaurate, mixed diesters, said mixed diesters having acyl groups selected from stearoyl, palmitoyl, cocoyl, lauroyl where both acyl groups are not the same, and mixtures thereof.

5. A topical cosmetic or dermatological composition according to claim 4 wherein the sucrose monoester and the sucrose diester are sucrose esters having the same acyl group.

6. A topical cosmetic or dermatological composition according to claim 3 wherein the at least one solid fatty alcohol is a mixture of cetyl and stearyl alcohol in a weight/weight ratio of from about 30:70 to about 70:30.

7. The composition according to claim 3 which is a lotion having a viscosity of from about 7,500 cps to less than about 20,000 cps (LV14@12 rpm) or a cream having a viscosity of from about 20,000 cps to about 50,000 cps (LV14@12 rpm).

8. A composition according to claim 3, which is a vehicle for immediate or sustained delivery of active ingredients to the skin.

9. A composition according to claim 3, which is a skin moisturizer, a skin protectant, or a water-resistant sunscreen.

10. A method of cosmetically treating the skin, comprising applying the composition of claim 3 to the skin.

11. A cosmetic or dermatological composition according to claim 3 wherein the emulsion is comprised of an oil phase of from about 5% to about 35% by weight relative to the total weight of the emulsion and a water phase of from about 65% to about 95% by weight relative to the total weight of the emulsion.

12. A cosmetic or dermatological composition according to claim 11 wherein a phytosterol is present at concentrations from about 0.05% to about 0.5% by weight relative to the total weight of the emulsion.

13. A cosmetic or dermatological composition according to claim 12 wherein the phytosterol is beta sitosterol.

14. A method of pharmacologically treating the skin, comprising applying the composition of claim 3 to the skin.

15. A process for making a cosmetic or dermatological composition having a multi-lamellar liquid crystalline network in an oil-in-water emulsion comprising the steps of:
   (a) combining a first sucrose ester source that is predominantly a sucrose monoester and a second sucrose ester source that is predominantly a sucrose diester to obtain an emulsifier system in which the ratio, by weight of monoester to diester is about 1:1.33;
   (b) preparing an outer water phase;
   (c) preparing an inner oil phase;
   (d) hydrating the emulsifier system in said outer water phase; and
   (e) adding the oil phase to the water phase.

* * * * *